United States Patent [19]
Guba et al.

[11] Patent Number: 4,894,854
[45] Date of Patent: Jan. 16, 1990

[54] SIZE SENSING X-RAY CASSETTE TRAY

[75] Inventors: Robert F. Guba, Orange, Conn.; Karl Leschanz, New Rochelle, N.Y.

[73] Assignee: Varian Associates, Inc., Palo Alto, Calif.

[21] Appl. No.: 187,206

[22] Filed: Apr. 28, 1988

[51] Int. Cl.$^4$ .............................................. G03B 42/02
[52] U.S. Cl. ...................................... 378/181; 378/167
[58] Field of Search ............... 378/181, 182, 177, 167, 378/171–174

[56] References Cited

U.S. PATENT DOCUMENTS

| | | | |
|---|---|---|---|
| 3,518,435 | 11/1967 | Kok | 378/181 |
| 3,764,808 | 10/1973 | Lackey et al. | 378/181 |
| 3,792,283 | 2/1974 | Lebra | 378/181 |
| 3,826,922 | 7/1974 | Ingles | 378/181 |
| 3,986,034 | 10/1976 | Wittkopp et al. | 378/181 |
| 4,137,460 | 1/1979 | Fitzsimmons et al. | 378/181 |
| 4,232,227 | 11/1980 | Finkenzeller et al. | 378/181 |
| 4,416,020 | 11/1983 | Wagner et al. | 378/181 |

Primary Examiner—Craig E. Church
Attorney, Agent, or Firm—Stanley Z. Cole; John C. Yakes

[57] ABSTRACT

A size sensing X-ray cassette tray having a pair of longitudinally spaced opposing front and back cassette clamps linked together by a center pivoted arm and link members for unison movement. A side sensing arm is connected by an elongatable link member to a pivoted leg which is actuated by a probe of an X-ray system. Arcuate potentiometers are coupled to the pivoted arm and the side sensing arm so as to provide electric signals corresponding to the x and y dimensions of a mounted cassette. The potentiometers are nonlinear so as to provide respective cosine and sine correction and thereby make the output signals substantially linear with the dimensions of sensed cassettes.

3 Claims, 5 Drawing Sheets

SIZE SENSING X-RAY CASSETTE TRAY

BACKGROUND OF THE INVENTION

The invention generally relates to X-ray apparatus, and more particularly relates to size sensing X-ray cassette trays that are used with X-ray collimation systems to adjust the size of the X-ray beam in accordance with the size of the X-ray cassette mounted on the tray.

With X-ray systems, it is common to use X-ray cassettes that mount on X-ray trays or holders. More specifically, the unexposed film or other sensitive material is placed inside a rectangular cassette that is positioned on a cassette tray. In order to center and hold cassettes of various different sizes, trays typically have front and back clamps that slide in unison toward and away from the center of the tray. The loaded cassette tray is then inserted into the X-ray system.

As is well known, it is desirable to adjust or collimate the X-ray beam to the size of the film being used so as to avoid unnecessary radiation. For this purpose, it has been common to use X-ray trays that sense the size of the cassette so that the system can automatically collimate the beam in accordance therewith. Once such system is described in U.S. Pat. No. 4,416,020. The cassette tray has a straight linear potentiometer that runs adjacent and parallel to the slide track of the clamp. The wiper of the potentiometer is mounted to the slide of the clamp such that the electric potential at the output of the potentiometer is directly related to the length of the X-ray cassette that is clamped. Similarly, a side sensing finger moves in a straight slot that is orthogonal to the clamp slide, and a second straight linear potentiometer runs adjacent and parallel to the slot. Accordingly, the second potentiometer provides an electric potential that is directly related to the width of the X-ray cassette. With such arrangement, however, the straight potentiometers must be relatively long so as to be able to sense the dimensions of the smallest and the largest cassette sizes. Further, there may be a tendency for the wipers to bounce because they are mounted to slides, and such tendency increases with age of the tray. Another disadvantage is that the potentiometers are adjacent to the open slots and therefore are subject to environmental conditions that can cause degradation of the electrical contact. Also, the mechanical linkage which drives the sensing finger in a straight slot from a rotating arm may be unreliable and subject to sticking or jamming.

Another prior art approach is described in U.S. Pat. No. 3,764,808. The side sensing finger moves in an arcuate path thereby eliminating a mechanical linkage between a rotating arm and a straight slot sensor. However, recognizing that the setting of a rotary potentiometer is linearly related to the sine of the angle formed by the side of the cassette and a line from the point of contact of the sensing finger through the pivot post, mechanical compromises were made in an attempt to minimize the nonlinearity between the potentiometer setting and the cassette dimensions. For example, the pivot point was selected so as to keep the angle small so as to minimize the deviation from linearity. However, such apparatus only partially compensates for the sine error.

SUMMARY OF THE INVENTION

It is an object of the invention to provide an improved size sensing mechanism for an X-ray cassette tray.

It is also an object to provide a size sensing X-ray cassette tray that provides output signals that are substantially linearly proportional or directly related to the x and y dimensions of the X-ray cassette. Further, it is an object to provide such apparatus using simplified and reliable mechanical linkages for the dimension sensors.

It is a further object to use nonlinear arcuate potentiometers coupled to rotating arms of reliable size sensing apparatus to provide correction or at least partially compensate for sine error and thereby provide output signals that are substantially linearly proportional or directly related to the dimensions of the cassettes being sensed.

It is a further object to use a finger actuation and release mechanism that has a highly reliable longitudinally elongatable link between the finger sensing arm and a rotatable leg that is actuated by the actuation probe of an X-ray system.

In accordance with the invention, these and other objects are provided by apparatus for sensing the size of an X-ray cassette mounted on an X-ray cassette tray comprising a size sensor adapted for movement to contact a side of an X-ray cassette mounted on the tray, a pivoted arm coupled to the sensor and rotationally responsive to movement of the sensor wherein the angular position of the pivoted arm corresponds to the position of the sensor, and a nonlinear potentiometer coupled to rotate with the pivoted arm for providing a signal corresponding to the dimension of a cassette contacted by the sensor, the potentiometer comprising means for providing correction for the nonlinearity between the motion component of the sensor in the direction of the cassette dimension and the resulting angular rotation of the pivoted arm so that the signal provided by the potentiometer is substantially linearly proportional to cassette dimensions. It may be preferable that the sensor be connected to the end of the pivoted arm. Alternately, it may be preferable that the sensor comprise a pair of clamps and the apparatus further comprise link members connecting one end of each of the clamps to opposite ends of the pivoted arm. It is preferable that the correcting means comprise a flat arcuate resistive track having substantially equal resistances between sequential arcs of different lengths, the arcs corresponding to unitary steps of the sensor in the direction of the cassette dimensions. It may be preferable that the track be mounted to the cassette tray and the potentiometer further comprise a wiper coupled to rotate with the pivoted arm while engaging the resistive track. With such arrangement, the potentiometer provides correction for the nonlinearity between the motion of the sensor and the rotation of the pivoted arm thereby providing an output signal that is substantially linearly proportional to the cassette dimensions.

The invention may also be practiced using a size sensing X-ray tray comprising a tray, an arm pivoted to the tray, the arm having one end adapted for rotating in a first direction to contact a side of the X-ray cassette mounted on the tray, a leg pivoted to the tray, a link member having one end pivotally connected to the arm and a second end pivotally connected to the leg, a first spring for urging the link member towards the arm for rotating the arm in a second direction away from the X-ray cassette, the pivoted leg being adapted for rotation by a probe of an X-ray system when the X-ray tray is inserted into the X-ray system whereby the leg exerts a force on the link member which overcomes the first spring and urges the link member to rotate the arm in the first direction until the arm contacts the X-ray cassette, and the link member comprises a resilient member for expanding the length of the link member so that the leg member can continue to rotate after the arm is stopped by the X-ray cassette.

BRIEF DESCRIPTION OF THE DRAWINGS

The foregoing objects and advantages of the invention will be more fully understood by reading the Description of the Preferred Embodiment with reference to the drawings wherein.

DESCRIPTION OF THE PREFERRED EMBODIMENT

With general reference to the drawings, size sensing X-ray cassette tray 10 includes front-to-back movable clamps 16 for centering and holding an X-ray cassette 12. Clamps 16 also function as sensors for the clamped dimension of cassette 12, and side sensing finger 34 moves to contact one side 38 of cassette 12 so as to function as a sensor for the orthogonal dimension of cassette 12. Side sensing finger 34 is coupled to pivoted side sensing arm 44 and clamps 16 are linked to pivoted center arm 102 such that the angular position of pivoted arms 44 and 102 respectively correspond to the orthogonal dimensions of cassette 12. Pivoted arms 44 and 102 each have a respective potentiometer arm 86 and 110 with wipers 92a and b and 112a and b coupled thereto, with respective potentiometers 88 and 116 mounted to the main panel 13. Through electrical connector 40, the X-ray collimation system provides an electric potential to potentiometers 88 and 116, and then senses the respective outputs so as to determine the dimensions of cassette 12. However, because of the trigonometric relationships between sensors and pivoted arms 44 and 102, the potentiometer wiper motions are not linearly proportional to cassette dimensions. In order to provide sine correction in the case of potentiometer 88 and cosine correction in the case of potentiometer 116 so as to improve linearity between cassette dimensions and output signals, potentiometers 88 and 116 have suitable arranged nonlinear resistive tracks 90a and 114a. By making the linearity correction in the potentiometers 88 and 116 rather than by making mechanical compromises, a simple and reliable size sensing mechanism is provided.

Figure 1:
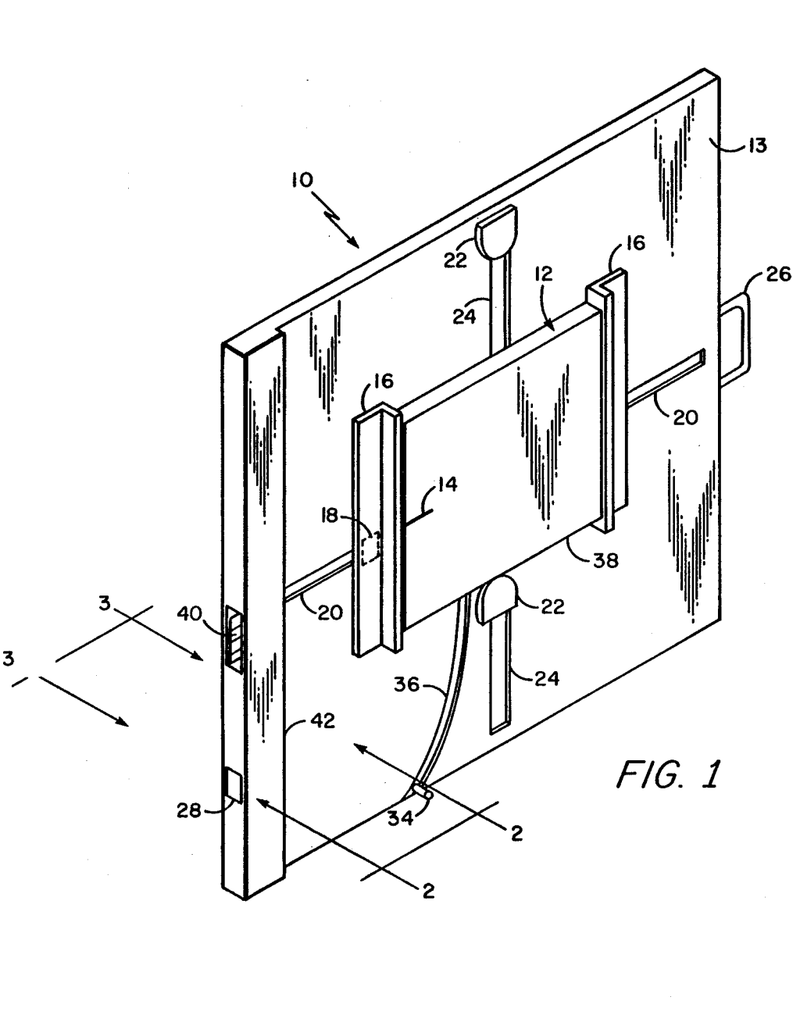
FIG. 1 is a perspective view of a size sensing X-ray cassette tray with a mounted cassette.

Referring now to the specific figures wherein like referenced characters designate corresponding parts throughout the several figures, FIG. 1 illustrates an X-ray cassette tray 10 or holder adapted for insertion in an X-ray collimator system such as an X-ray table. As is well known, X-ray cassette 12 which may be of a variety of standard sizes, is first prepared by inserting therein unexposed film or similar sensitive material. Then, the loaded film cassette 12 is positioned on the main panel 13 of X-ray cassette tray 10 with the vertical position being determined by visually aligning a locator mark 14 on the X-ray cassette 12. Herein, direction adjectives such as vertical, horizontal, up or down are with reference to the figures and not to the Earth, as it should be understood that the cassette tray 10 can be loaded or operationally used in various different orientations. Next, front-to-back cassette clamps 16 which have slides 18 coupled to horizontal slots 20 are adjusted to seat against the respective front and back edges of X-ray cassette 12. As will be described later herein, clamps 16 are linked to move in unison towards and way from each other such that when the clamps 16 contact the respective edges of a cassette 12, the cassette is centered on tray 10. Vertical slide support members 22 are positioned in vertical slots 24 and, if the cassette tray 10 is to be used in a vertical orientation as shown in FIG. 1, the bottom support member 22 is slid upwardly to cassette 12 and locked in place so as to provide support.

X-ray cassette tray 10 has a handle 26 which is used for inserting and removing cassette tray 10 from an X-ray collimator system such as an X-ray table. Cassette tray 10 has a front aperture 28 which, when inserted in a collimator system, receives a probe 30 (FIG. 2) or actuator. As will be described in detail later herein, probe 30 actuates the side sensing finger actuation and release mechanism 32 (FIG. 2) which causes sensing finger 34 to travel in arcuate slot 36 up to and against the side 38 of X-ray cassette 12.

Cassette tray 10 also has an electrical connector 40 which mates with a corresponding connector (not shown) when inserted in a collimator system and, as will be described in detail later herein, electrical connector 40 is used to transfer to the collimator system electrical signals indicating the x and y dimensions of the X-ray cassette 12. More specifically, these signals indicate the position of front-to-back clamps 16 for the x dimension and the position of side sensing finger 34 for the y dimension. In response to these signals which are substantially linear with respect to sensed dimensions of the X-ray cassette 12, the collimator system, in accordance with well-known practice, adjusts or collimates the X-ray field size to match the size of the X-ray cassette 12 being used.

Figure 2:
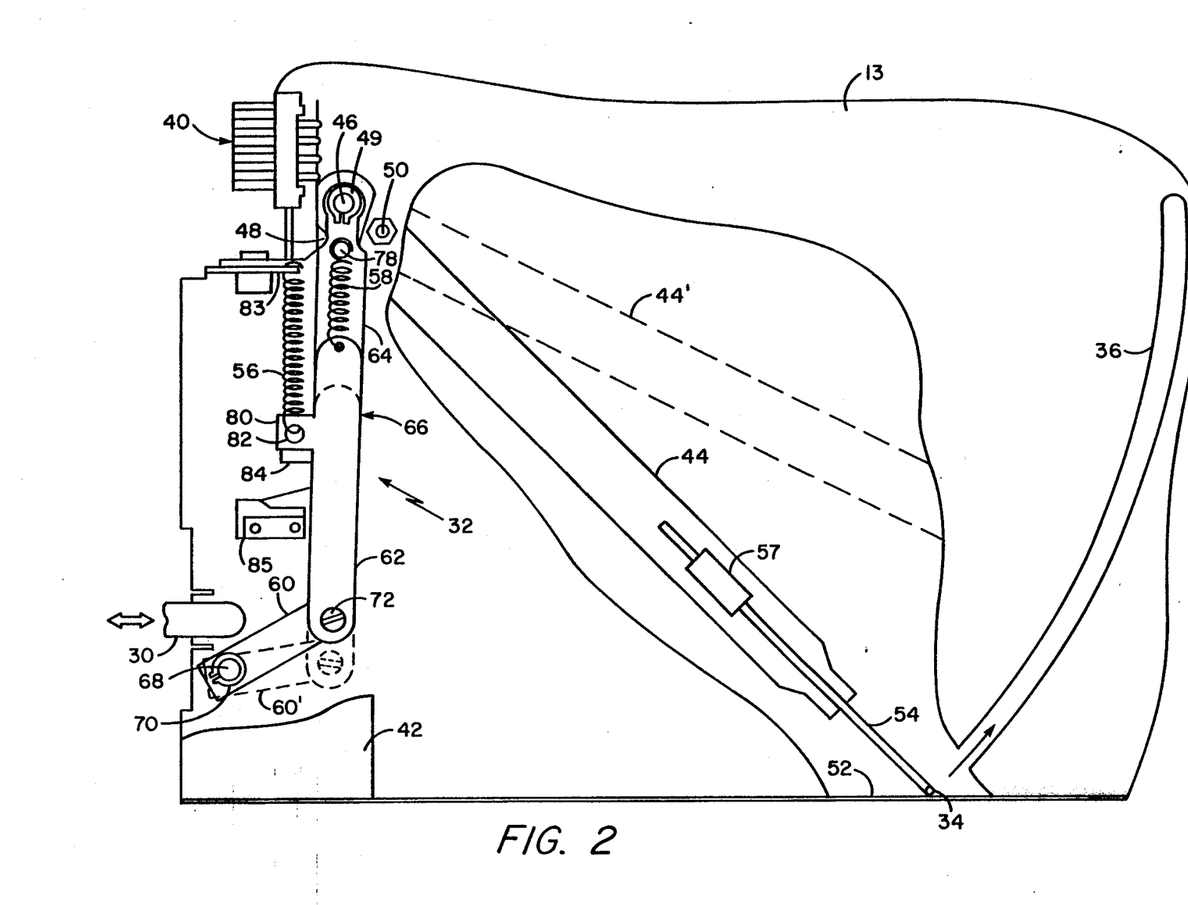
FIG. 2 is a view taken along line 2—2 of FIG. 1 with portions broken away.

Referring to FIG. 2, there is shown a view taken along line 2—2 of FIG. 1 with switch cover 42 and a portion of the main panel 13 of cassette tray 10 broken away. As shown, side sensing finger actuation and release mechanism 32 is located under switch cover 42 on the facing side of main panel 13, and rotating side sensing arm 44 for side sensing finger 34 is located on the opposite side of main panel 13. Mechanism 32 and side sensing arm 44 are interconnected by pivot pin 46 which extends through a notch 48 in main panel 13 such that pivot pin 46 can freely move in the y direction. Grip ring 49 secures mechanism 32 to pivot pin 46. Side sensing arm 44 is pivotally mounted to post 50 which is affixed to main panel 13. Accordingly, when mechanism 32 exerts an upward force on pivot pin 46, side sensing arm 44 is urged in the clockwise or outward direction against the side 52 of cassette tray 10 as shown in FIG. 2. However, when mechanism 32 exerts a downward force on pivot pin 46, side sensing arm 44 is urged to rotate about pivot post 50 in a counterclockwise direction toward the center of X-ray cassette tray 10 as shown by the dotted arm 44'. In such rotating, side sensing finger 34, which is a right-angle bend from a wire 54 attached to side sensing arm 44 by bracket 57, travels in arcuate slot 36 towards X-ray cassette 12. Thus, mechanism 32 controls the angular position of side sensing arm 44 and sensing finger 34.

Figure 5:
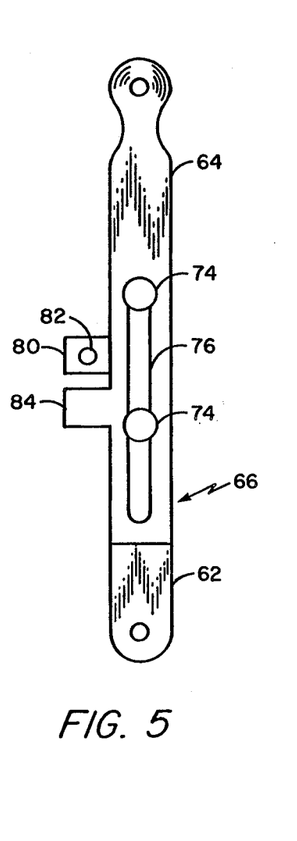
FIG. 5 is a bottom view of the elongatable link arm for the side sensing finger.
Figure 6:
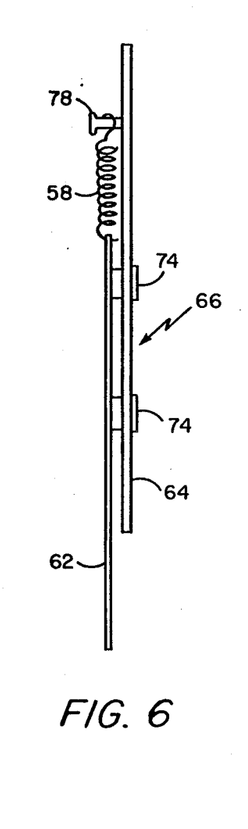
FIG. 6 is a side view of the elongatable link arm of the side sensing arm.

Still referring to FIG. 2, side sensing finger actuation and release mechanism 32 includes a pair of springs 56 and 58, a rotatable leg 60, and a pair of longitudinally coupled slide arms 62 and 64 which form an elongatable control arm 66 or link member. One end of rotatable leg 60 is pivotally connected to pivot post 68 which is affixed to main panel 13. Rotatable leg 60 is secured in place by grip ring 70. The opposite end of rotatable leg 60 is pivotally connected to upper slide arm 62 by pivot pin 72. As shown in FIGS. 5 and 6 which are bottom and side views of elongatable control arm 66, upper slide arm 62 has a plurality of projecting slide bosses 74 which insert and are secured in a slot 76 of lower slide arm 64 thereby longitudinally disposing slide arm 62 over slide arm 64 in sliding engagement. Spring 58 is connected from the end of upper slide arm 62 to a post 78 on slide arm 64. Thus, elongatable control arm 66 or link member can be elongated or lengthened by exerting a force on the opposing ends to overcome the tension of spring 58 thereby allowing slide bosses 74 to slide longitudinally within slot 76.

Slide arm 62 has a lateral projection or wing 80 with a hole 82 into which one end of spring 56 is inserted. The opposite end of spring 56 is attached to a bracket 83 on the cassette tray 10. In the position as shown with the solid lines in FIG. 2, spring 56 urges wing 80 and upper slide arm 62 in an upward direction such that the forward slide boss 74 of slide arm 62 pushes against the end of slot 76 thereby urging lower slide arm 64 to exert an upward force on pivot pin 46 with spring 58 in a compressed state. Such force on pivot pin 46 urges side sensing arm 44 to rotate in the clockwise direction to the outward or released position with side sensing finger 34 against side 52 as shown. In this released or outward position of side sensing finger 34, X-ray cassettes 12 may be freely mounted or unmounted from X-ray cassette tray 10 without side sensing finger 34 interfering.

When cassette tray 10 is inserted in an X-ray collimation system, a probe 30 or actuator inserts into front aperture 28 and contacts rotatable leg 60. As probe 30 inserts further, it causes rotatable leg 60 to rotate clockwise about pivot post 68 toward the dotted rotatable leg 60'. Such rotation forces upper slide arm 62 downwardly notwithstanding the tension force applied on wing 80 by spring 56. In other words, the force of spring 56 is overcome and upper slide arm 62 moves downwardly. Spring 58 has a relatively high spring constant (i.e. low compliance), so as upper slide arm 62 moves downwardly, spring 58 does not stretch but remains compressed thereby pulling lower slide arm 64 downwardly. Such downward force on pivot pin 46 causes side sensing arm 44 to rotate counterclockwise about pivot post 50 towards the center of the cassette tray 10 as shown by dotted sensing arm 44'. As a result, side sensing finger 34 which protrudes up through arcuate slot 36 travels inwardly in arcuate slot 36 until it contacts the side 38 of X-ray cassette 12, at which point further rotation of side sensing arm 44 is prevented. As probe 30 continues to further rotate rotatable leg 60 after side sensing finger 34 has engaged X-ray cassette 12 thereby preventing pivot pin 46 from moving downwardly, the relatively high spring constant of spring 58 is overcome and it stretches thereby permitting elongatable control arm 66 or link member to lengthen so that cassette tray 10 can be fully inserted into the X-ray collimation system. Thus, the presence of spring 58 prevents mechanical damage to rotatable leg 60 and elongatable control arm 66 when side sensing finger 34 engages the side 38 of the X-ray cassette 12 before the cassette tray 10 is fully inserted into the X-ray system. When the X-ray cassette tray 10 is removed from the X-ray system such that probe 30 no longer exerts a force on rotatable leg 60, spring 56 again pulls upper slide arm 62 upwardly thus releasing the rotating side sensing arm 44 so that side sensing finger 34 travels to side 52.

In the event that a cassette 12 is not mounted on cassette tray 10 when it is inserted in an X-ray system and side sensing finger 34 is activated by probe 30, there is nothing to prevent side sensing finger 34 from traveling the entire length of arcuate slot 36. In such case, lower slide arm 64 continues downwardly without spring 58 stretching such that a projection or wing 84 from the side of lower slide arm 64 contacts microswitch 85. Closing of microswitch 85 provides an indication to the X-ray collimation system that no X-ray cassette 12 is present, and the system is disabled.

Figure 3:
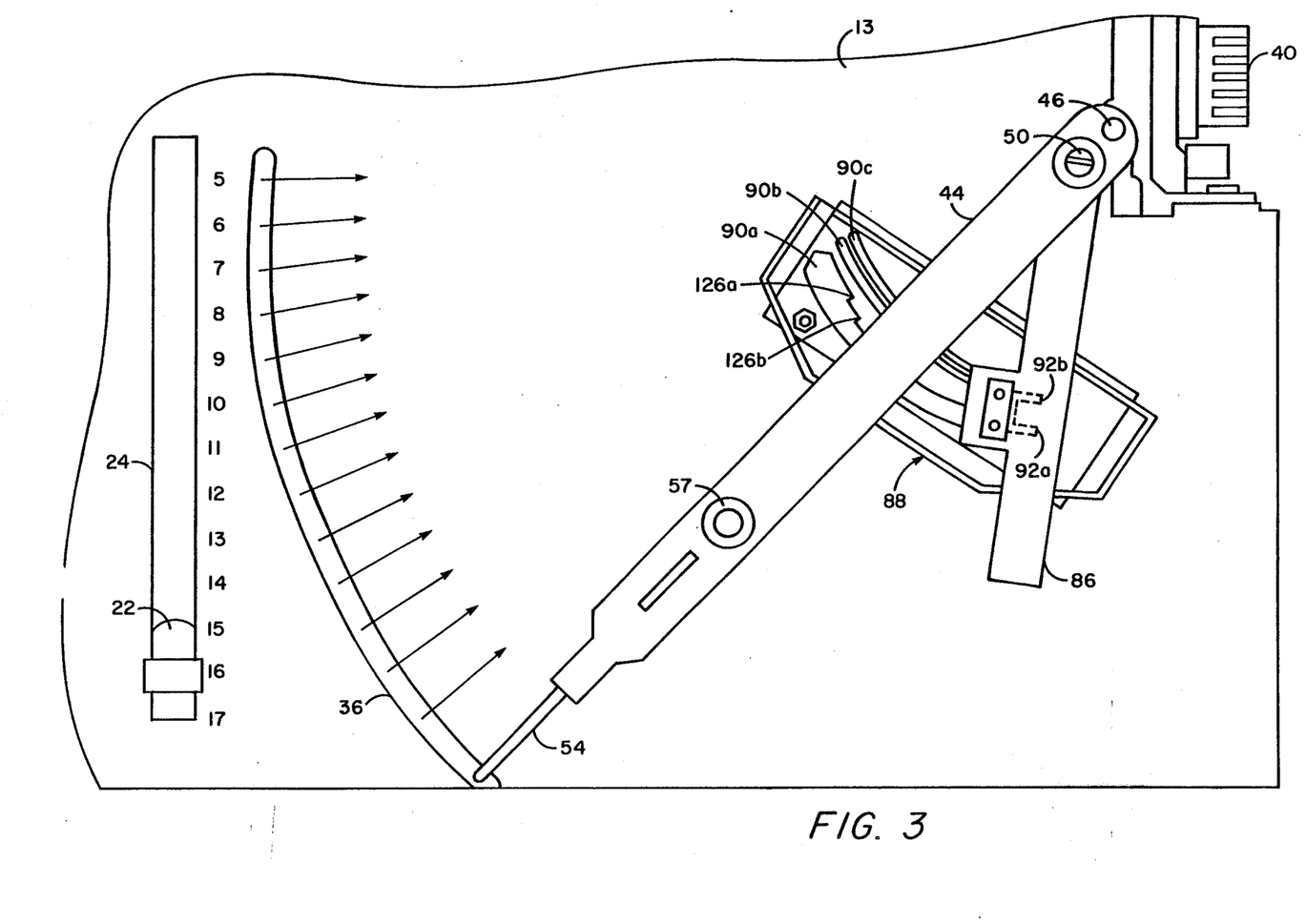
FIG. 3 is a view taken along line 3—3 of FIG. 1.

Referring to FIG. 3, there is shown a view taken along lines 3—3 of FIG. 1 illustrating the opposite side of rotating side sensing arm 44. Potentiometer arm 86 is connected to pivot post 50 and rotates concentrically with rotating side sensing arm 44. Potentiometer arm 86 and side sensing arm 44 are coupled such that the angle between them is fixed. In other words, as sensing arm 44 rotates through a particular arc, potentiometer arm 86 rotates through the same arc. Potentiometer 88 includes a plurality of flat arcuate tracks 90a–c mounted to main panel 13, and potentiometer wipers 92a and b mounted to potentiometer arm 86. As side sensing arm 44 rotates thus rotating potentiometer arm 86, potentiometer wipers 92a and b travel along tracks 90a and c thus changing the internal resistance of potentiometer 88 as will be described in detail later herein.

Figure 4:
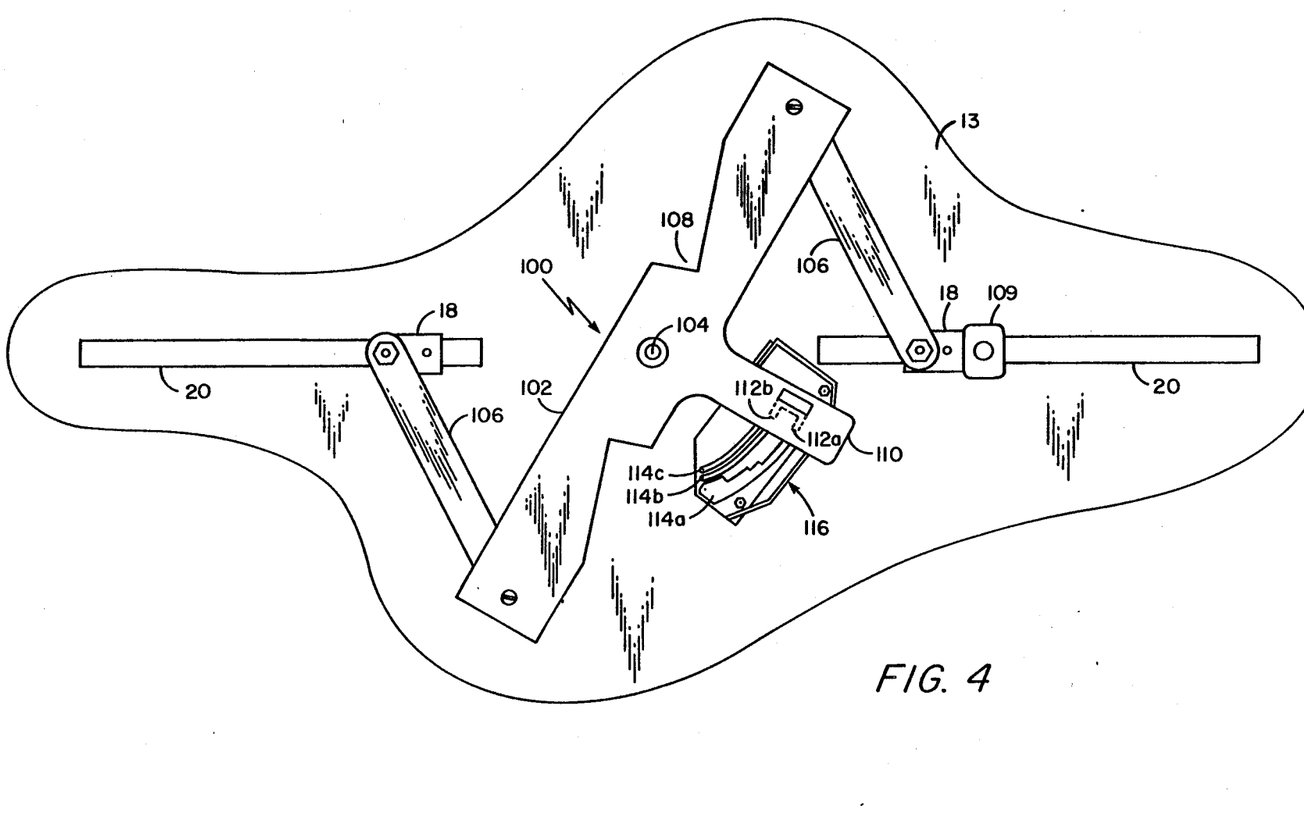
FIG. 4 is a view of the scissors link mechanism on the opposite side of the tray as shown in FIG. 1.

FIG. 4 is a opposite side view of cassette tray 10 of FIG. 1 showing scissors mechanism 100 which is coupled to front-to-back clamps 16 (FIG. 1). Slides 18 are connected to front-to-back clamps 16 and are slidable engaged in horizontal slots 20 such that they can be horizontally slid along horizontal slots 20. Scissors mechanism 100 includes pivot or center arm 102 which is pivotally connected to main panel 13 at fixed pivot post 104 and a pair of link arms 106 each of which has one end pivotally connected to respective ends of center arm 102 and the opposite end pivotally connected to respective ones of slides 18 as shown. Accordingly, as front-to-back clamps 16 are slid laterally along horizontal slots 20 so as to adjust to the size of an X-ray cassette 12, the motion of slides 18 and link arms 106 causes a scissors action which rotates center arm 102 about pivot post 104. It is noted that because of the symmetrical arrangement of scissors mechanism 100 as shown, slides 18 and therefore front-to-back clamps 16 are always equidistant from center post 104 such that X-ray cassette 12 is always front-to-back centered over pivot post 104. The sides of center arm 102 have notches 108 which permit support members 22 to be slid towards the center of cassette tray 10 when scissors mechanism 100 is in a closed configuration. Front-to-back clamps 16 are provided with a lock 109 to prevent slides 18 from moving along horizontal slots 20 after a cassette 12 is secured.

Still referring to FIG. 4, center arm 102 has a perpendicularly projecting potentiometer arm 110 which has potentiometer wipers 112a and b mounted to the underside thereof. Wipers 112a and b contact respective flat arcuate tracks 114a and c of arcuate nonlinear potentiometer 116 which is mounted to main panel 13 facing wipers 112a and b. As center arm 102 rotates about pivot post 104 in response to the scissors action of link arms 106, potentiometer arm 110 also rotates about pivot post 104 causing potentiometer wipers 112a and b to travel along potentiometer tracks 114a and c.

In operation, when an X-ray cassette 12 is positioned on X-ray cassette tray 10 in a vertically centered orientation, the operator slides front-to-back clamps 16 up against the front and back edges of X-ray cassette 12. Such motion of front-to-back clamp 16 rotates scissors mechanism 100 as described heretofore, thus positioning potentiometer wipers 112a and b in an angular position corresponding to the front-to-back dimensions of X-ray cassette 12. Then, when X-ray tray 10 is inserted in an X-ray collimation system, probe 30 activates side sensing finger actuation and release mechanism 32 thus moving side sensing finger 34 to the side 38 of X-ray cassette 12 as described heretofore. Such motion of side sensing finger 34 moves potentiometer wipers 92a and b along tracks 90a and c of potentiometer 88 to an angular position corresponding to the side dimension of X-ray cassette 12. Through electrical connector 40 the X-ray collimation system provides an electrical voltage to potentiometers 88 and 116, and then senses the output signals so as to determine the angular position of wipers 92a and 112a which correspond to the side-to-side and front-to-back dimensions of X-ray cassette 12. According to conventional practice, the X-ray collimation system then adjusts or collimates the X-ray field size according to the size of the X-ray cassette 12 so as to eliminate unnecesary radiation.

In accordance with the invention, the signals or voltages provided by potentiometers 88 and 116 are substantially linearly proportional to the respective y and x dimensions of cassettes 12, even though the angular rotations of pivoted arms 44 and 102 are not linearly proportional to such dimensions. More specifically, referring to FIG. 3, numerals representative of the y dimensions of cassette 12 are illustratively shown in a vertical column adjacent to vertical slot 24. Such dimensions may, for example, be in inches. It is noted, however, that the spacing between sequential dimension markers would be half of the dimension unit or 0.5 inches because cassettes are vertically centered on main panel 13 such that half of any increase in dimension goes to the bottom while the other half goes to the top. Also shown are radial arrows which, for illustration, are directed from the point of contact of side sensing finger 34 with the various cassette sizes to pivot post 50 about which side sensing arm 44 rotates. It can be seen that although the cassette dimension markers are equally or linearly spaced, the corresponding rotational angles or arc increments of side sensing arm 44 are not equal or linear. In other words, the arc increments of sensing arm 44 and accordingly potentiometer arm 86 vary as the sine of the angle rather than linearly with the dimensions of the cassettes. More specifically, as can be seen in Table 1 below which was calculated for an 8.5 inch pivot arm 44, the arcs corresponding to unitary cassette dimension steps are larger for the larger cassette sizes.

TABLE I

| CASSETTE DIMENSION | ANGLE OF WIPER | RESISTANCE FROM LOW SIDE TERMINAL |
|---|---|---|
| 5 | 2.50° | 60 |
| 6 | 5.85 | 133 |
| 7 | 9.25 | 206 |
| 8 | 12.70 | 279 |
| 9 | 16.20 | 352 |
| 10 | 19.75 | 425 |
| 11 | 23.35 | 498 |
| 12 | 27.10 | 571 |
| 13 | 30.95 | 644 |
| 14 | 34.95 | 717 |
| 15 | 39.20 | 790 |
| 16 | 43.70 | 863 |
| 17 | 48.55 | 936 |

Rather than using mechanical compromises in an attempt to minimize sine and cosine errors so as to increase the linearity between the output of potentiometers 88 and 116 and the dimensions of the cassettes 12, the invention uses simple and reliable cassette size sensing apparatus and provides sine and cosine correction by using potentiometers 88 and 116 that are suitably nonlinear. More specifically, potentiometer 88 has nonlinear resistance such that for unitary increases in the y dimension of a cassette 12, there are corresponding equal increases in resistance even though the arcuate length per cassette dimension unit varies depending on the angle of the wiper 92a from rotating post 50. For example, referring to Table I above, there are approximately 73 ohms of resistance between each of the angles corresponding to cassette dimension units.

Figure 7:
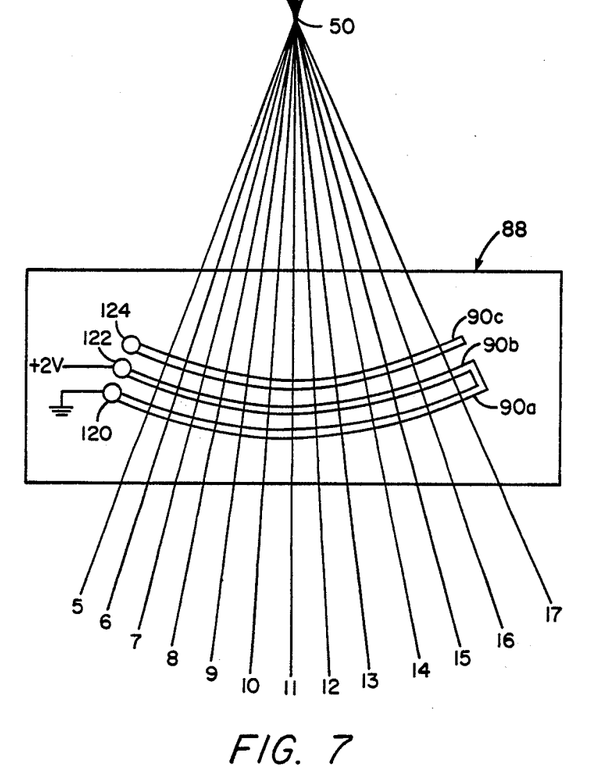
FIG. 7 is a diagrammatical view of a nonlinear potentiometer.

FIG. 7 shows a diagrammatical representation of potentiometer 88. Track 90a is an approximately 50° arcuate line having 1,000 ohms of nonuniform or nonlinear resistance. Terminal 120 is the low side of potentiometer 88 and is grounded. Terminal 122 is the high side of potentiometer 88 and X-ray collimation system provides a suitable sensing voltage such as, for example, +2 volts, through electrical connector 40 to terminal 122. Track 90b is a short circuit and merely functions to connect the +2 volts to the right end of track 90a from conveniently located terminal 122. Wiper 92a moves along track 90a and, because there are substantially equal resistances (eg.—73 ohms as shown in Table I) between the angular positions corresponding to unitary cassette dimensions, wiper 92a picks off a voltage that is substantially linearly proportional to the y dimension of the sensed cassette. For example, between each sequential angular position corresponding to a unitary cassette dimension, there is a voltage drop of approximately (73÷1000)×2 or 0.146 volts. Wiper 92b is electrically connected to wiper 92a and track 90c is a short circuit line which functions as a slip ring or collector strip to transfer the voltage picked off of track 90a by wiper 92a to convenient terminal 124.

Figure 8:
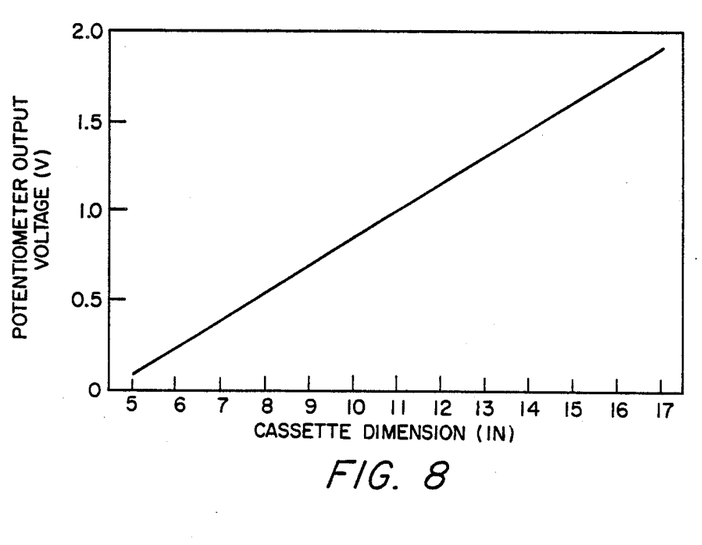
FIG. 8 is a graph of the output characteristic of the potentiometer.

FIG. 8 shows the output characteristic of potentiometer 88 as plotted against the cassette dimensions. As can be seen from FIG. 8, when the wiper 92a is to the right of track 90a so as to sense a large cassette such as 17 inches, there is very little resistance or voltage drop from the 2.0 volt input, so the sensed voltage approaches or is slightly less than 2 volts. When wiper 92a is to the left end of track 90a near grounded terminal 120, the sensed voltage is relatively small. In between these two end points for side sensing finger 34, the sensed voltage is substantially linearly proportional to the cassette dimensions because there are substantially equal resistances between arcuate positions which correspond to the cassette dimensions. In other words, the nonlinearity of potentiometer track 92a provides correction for the nonlinearities of the sine angle of rotating arm 44.

Those skilled in the art will recognize that although the angles and resistances in Table I mathematically provide sine correction, it would be difficult to fabricate a flat nonlinear potentiometer to such precise accuracy. Furthermore, the tolerances are not critical, especially in the region where the angle is relatively small such that the deviation in resistance to unit length is also small. Accordingly, in a practical embodiment of potentiometer 88, the resolution on the cassette dimensions or unitary steps as shown in Table I may be decreased such that the thirteen graduations as shown could be placed into two or three groupings each having a corresponding resistance per arcuate length. For example, in FIG. 3, see steps 126a and b in track 90a which represent transitions between nonlinear resistance. Accordingly, the output characteristic or voltage response for potentiometer 88 would not be so linear as shown in FIG. 8, but rather would have incremental steps. Such steps could still provide acceptable sine correction.

Similar to the sine correction potentiometer 88 provides between the motion of side sensing finger 34 in the y direction and rotation of wiper 92a, potentiometer 116 provides cosine correction between the motion of clamps 16 and rotation of wiper 112a. The angular positions of wiper 112a on potentiometer 116 for various x dimensions of cassettes 12 can be determined trigonometrically or by actual measurement. As an example, Table II below provides acceptable cosine correction for a scissors mechanism 100 having 2.5 inches between pivot points of link members 106, and 10.5 inches between pivot points on pivoted arm 102.

TABLE II

| CASSETTE DIMENSION | ANGLE OF WIPER | RESISTANCE FROM LOW SIDE TERMINAL |
|---|---|---|
| 5 | 2.5° | 60 |
| 6 | 5.25 | 133 |
| 7 | 8.0 | 206 |
| 8 | 11.0 | 279 |
| 9 | 14.0 | 352 |
| 10 | 17.25 | 425 |
| 11 | 20.5 | 498 |
| 12 | 24.0 | 571 |
| 13 | 27.5 | 644 |
| 14 | 31.0 | 717 |
| 15 | 35.0 | 790 |
| 16 | 40.25 | 863 |
| 17 | 45.5 | 936 |

It is noted that for illustration, a number of the sequential arc steps for wiper 112a are equal. For example, there is a 2.75° of arc between a 5 and 6 inch cassette, and also between a 6 and 7 inch cassette. Also, for example, there is 3.5° of arc between a 12 and 13 inch cassette, and also between a 13 and 14 inch cassette. In other words, rather than having a continuously varying resistance along track 114a, or having resistance that changes at unitary cassette dimensions, the length of track 114a can be divided into a few segments each having different resistances. In other words, depending on the degree of desired or needed trigonometric correction, more or fewer resistance steps can be used.

This concludes the description of the preferred embodiment. A reading of it by those skilled in the art will bring to mind many alterations and modifications without departing from the spirit and scope of the invention. Accordingly, it is intended that the invention be limited only by the appended claims.

What is claimed is:

1. An apparatus for sensing the length and width dimensions of a substantially rectangular X-ray cassette mounted on an X-ray cassette tray comprising:

front and rear cassette engaging clamp means slidably mounted on said tray for centering and holding an X-ray cassette on said tray;

linking means including a first arm pivotly mounted on said tray for enabling the movement in unison of said front and rear cassette engaging clamp means towards and away from each other;

a first potentiometer possessing a wiper attached to said first arm adapted to move in electrical contact with a flat arcuate resistive track mounted on said tray as said first arm rotates on its pivot, said first potentiometer having nonlinear output characteristics such that equal displacements of said front and rear cassette engaging clamp means result in substantially equal changes in resistance;

a second arm pivotly mounted on said tray having one end adapted for rotating to contact an unclamped side of an X-ray cassette held by said front and rear cassette engaging clamp means on said tray;

a second potentiometer possessing a wiper attached to said second arm adapted to move in electrical contact with a flat arcuate resistive track mounted on said tray as said second arm rotates on its pivot, said second potentiometer having nonlinear output characteristics such that equal increments in the distance between the unclamped sides of a substantially regular X-ray cassette held and centered on said tray result in substantially equal changes in resistance.

2. The apparatus of claim 1 wherein the flat arcuate resistive track of said first potentiometer comprises a plurality of sequential arcs of differing lengths each of which possesses a characteristic resistance per unit length so as to achieve an approximation of the desired nonlinear output characteristics.

3. The apparatus of claim 1 wherein the flat arcuate resistive track of said second potentiometer comprises a plurality of sequential arcs of differing lengths each of which possesses a characteristic resistance per unit length so as to achieve an approximation of the desired nonlinear output characteristics.

* * * * *